(12) United States Patent
Song

(10) Patent No.: US 8,691,844 B2
(45) Date of Patent: Apr. 8, 2014

(54) METHOD FOR TREATING THROMBOSIS AND INHIBITING PLATELET AGGREGATION WITH 21-(S)-ARGATROBAN

(75) Inventor: Honghai Song, Tianjin (CN)

(73) Assignee: Tianjin Weijie Technology Co., Ltd., Tianjin (CN)

( * ) Notice: Subject to any disclaimer, the term of this patent is extended or adjusted under 35 U.S.C. 154(b) by 0 days.

(21) Appl. No.: 13/450,443

(22) Filed: Apr. 18, 2012

(65) Prior Publication Data
US 2012/0202850 A1     Aug. 9, 2012

Related U.S. Application Data

(60) Division of application No. 12/565,838, filed on Sep. 24, 2009, now abandoned, which is a continuation of application No. PCT/CN2008/000690, filed on Apr. 3, 2008.

(30) Foreign Application Priority Data

Apr. 13, 2007   (CN) .......................... 2007 1 0057137

(51) Int. Cl.
*A01N 43/42*      (2006.01)
*A61K 31/47*      (2006.01)
*C07D 215/36*     (2006.01)

(52) U.S. Cl.
USPC ........................................ 514/314; 546/172

(58) Field of Classification Search
USPC ........................................... 514/314; 546/172
See application file for complete search history.

(56) References Cited

U.S. PATENT DOCUMENTS 5,141,947 A * 8/1992 Tamao et al. ................. 514/314

OTHER PUBLICATIONS

Kathiresan et. al., Journal of Thrombosis and Thrombolysis, 2002, Kluwer Academic Publishers, vol. 13, No. 1, pp. 41-47.*

* cited by examiner

*Primary Examiner* — Sarah Pihonak
(74) *Attorney, Agent, or Firm* — Matthias Scholl P.C.; Matthias Scholl

(57) ABSTRACT

A method for inhibiting coagulation including administering to a patient in need thereof a pharmaceutical composition containing 21-(S)-Argatroban and/or a pharmaceutically acceptable salt thereof. Compared with 21-(R)-Argatroban, 21-(S)-Argatroban significantly prolongs coagulation time of whole blood (CT), recalcification time (RT), kaolin partial thromboplastin time (APTT), pro-time prothrombin time (PT), thrombin time (TT), and reduces platelet adhesion rate and platelet aggregation rate in healthy dogs. Therefore, 21-(S)-Argatroban has a stronger effect for inhibiting coagulation and reducing therapeutically effective dose and is suitable for use in a method for treatment and/or prevention of thrombosis and inhibiting platelet aggregation.

4 Claims, No Drawings

METHOD FOR TREATING THROMBOSIS AND INHIBITING PLATELET AGGREGATION WITH 21-(S)-ARGATROBAN

CROSS-REFERENCE TO RELATED APPLICATIONS

This application is a divisional of U.S. Ser. No. 12/565,838 filed on Sep. 24, 2009 now pending, which is a continuation of International Patent Application No. PCT/CN2008/000690 with an international filing date of Apr. 3, 2008, which is based on Chinese Patent Application No. 200710057137.0, filed on Apr. 13, 2007. The contents of these specifications are incorporated herein by reference.

BACKGROUND OF THE INVENTION

1. Field of the Invention

The invention relates to a pharmaceutical composition and a use thereof, and more particularly to a pharmaceutical composition having 21-(S)-Argatroban and/or a pharmaceutically acceptable salt thereof and its use for inhibiting coagulation.

2. Description of the Related Art

Argatroban, i.e., (2R,4R)-1-((2S)-5-((Aminoiminomethyl)amino)-1-oxo-2-((1,2,3,4-tetrahydro-3-methyl-8-quinolinyl)sulfonyl)amino) pentyl)-4-methyl-2-piperidine carboxylic acid, has two diastereoisomers: 21(R) and 21(S). Usually the ratio of 21(R) to 21(S) is 64-65: 36-35 (U.S. Pat. No. 6,440,417, Cossy. J., et al, Bioorganic & Medicine Chemistry Letters, 11 (2001), 1989-1992, Journal of pharmaceutical Sciences, Vol. 82, No. 6, 672 (1993)).

The structure formula of Argatroban is reported below:

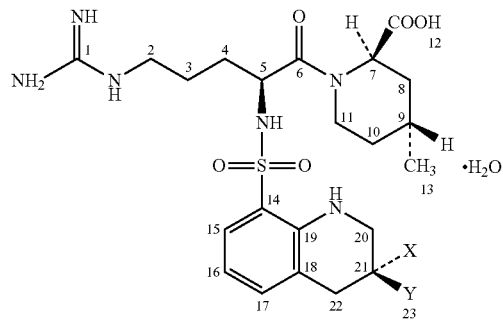

21(S) Argatroban, X=CH$_3$, Y=H;
21(R) Argatroban, X=H, Y=CH$_3$;
Argatroban, 21(S): 21 (R)=35:65.

The chemical names of the two diastereoisomers mentioned above are:
21(S) Argatroban: (2R,4R)-1-((2S)-5-((Aminoiminomethyl)amino)-1-oxo-2-((((3S)-1,2,3,4-tetrahydro-3-methyl-8-quinolinyl)sulfonyl)amino)pentyl)-4-methyl-2-piperidine carboxylic acid (121785-72-6); and
21(R) Argatroban: (2R,4R)-1-((2S)-5-((Aminoiminomethyl)amino)-1-oxo-2-((((3R)-1,2,3,4-tetrahydro-3-methyl-8-quinolinyl)sulfonyl)amino)pentyl)-4-methyl-2-piperidine carboxylic acid (121785-71-5).

As a derivative of L-arginine, Argatroban is a competitive inhibitor of thrombin and only interacts with active site of thrombin. It directly inactivates the activity of thrombin (clotting factor IIa) and has no direct action on the generation of thrombin. The function of Argatroban is independent of the anti-thrombin in body. Argatroban inactivates not only thrombin in free state in blood, but also inactivates the thrombin combined with fibrin thrombus, blocks the positive feedback of coagulation cascade, and inhibits the thrombin-induced platelet aggregation even in a very low concentration, which indirectly inhibits the formation of thrombin. Due to a small molecular weight, Argatroban can enter the inside of thrombus, directly inactivate the thrombin already combined with fibrin thrombus, and even exhibits an antithrombotic effect against an early-formed thrombosis. Furthermore, Argatroban can greatly decrease the level of thrombin-antithrombin complex (TAT) in plasma, effectively reduce the hypercoagulable state of patients, and has very good clinical results in treating chronic thromboembolic disease.

In 1978, S. Akamoto et al from Japanese Mitsubishi Chemical Corporation first disclosed the anti-thrombin activity of Argatroban monohydrate (U.S. Pat. No. 4,101,653). In the next 20 years, numerous researchers had in-depth studies on Argatroban about its biological activity and medicine values. In 1981, S. Akamoto compared Argatroban with heparin in vivo (Okamoto, S. et al., Biochem. Biophys. Res. Commun. 101, 440 (1981)); T. Kumoto disclosed its three-dimensional selective activity (Kumada, T. et al., Thromb. Res. 24, 285 (1981)). In 1984, R. Kumato made a clinical evaluation of hemodialysis of Argatroban (Kikumoto, R. et al., Biochemistry 23, 85 (1984)), and in 1986, he further disclosed that Argatroban can inhibit the thrombin activity of mammals, and can be used as active ingredient to treat and prevent thrombosis and as an inhibitor of platelet aggregation. Argatroban monohydrate can be used as a selective anti-thrombosis agent for treatment of chronic arterial blockage and cerebral thrombosis, etc (JP 61-48829). In 1992 and 1993, Taparelli and Jakubowski separately disclosed the reversibility of Argatroban in anti-thrombin (Taparelli, C., Trends Pharmacol. Sci., 1993, 14, 366, Jakubowski, J. A. et al, Rep. Med. Chem., 1992, 27, 99). In 1990s, many researchers such as L. R. Buch reported other related research (Buch, L. R., Cadiosvasc. Drug Rev., 1991, 9, 247, Strupcnewski, J. D. et al., Academic: San Diego, 1991; Vol. 26, p 299, Brundish, D. et al., J. Med. Chem. 1999; 42, 4584, Shebuski, R. J., Academic: San Diego, 1999; Vol. 26, p 98). In 1992, Argatroban monohydrate was first approved as an anti-thrombin medicine in Japan (Hijikata-Okunomiya, A., et al, Thromb. Hemostasis, 1992, 18, 135).

However, in recent years, countries around the world have stronger restrictions on drug ingredients. Besides individual impurity and total impurity amount, there are also strict restrictions on isomers of the active ingredients. Racemic active ingredient is a mixture consisting of isomers. In order to lower the therapeutically effective dose and reduce the side effect, replacing racemic isomers with highly effective single isomer is a trend in pharmaceutical area.

SUMMARY OF THE INVENTION

Therefore, in view of the above-described problems, it is one objective of the invention to provide a method for inhibiting coagulation that has a stronger effect of inhibiting coagulation and reducing therapeutically effective dose.

It is another objective of the invention to provide a pharmaceutical composition for inhibiting coagulation that has a stronger effect of inhibiting coagulation and reducing therapeutically effective dose.

In accordance with one embodiment of the invention, there provided is a method for inhibiting coagulation comprising administering to a patient in need thereof a pharmaceutical composition comprising 21-(S) Argatroban and/or a pharmaceutically acceptable salt thereof.

In accordance with another embodiment of the invention, further provided is a pharmaceutical composition for inhibiting coagulation comprising 21-(S) Argatroban and/or a pharmaceutically acceptable salt thereof.

In a class of this embodiment, the pharmaceutical composition for inhibiting coagulation further comprises an excipient.

In a class of this embodiment, the pharmaceutical composition for inhibiting coagulation further comprises 21(R) Argatroban and/or a pharmaceutically acceptable salt thereof.

In a class of this embodiment, the pharmaceutical composition for inhibiting coagulation further comprises an excipient and 21(R) Argatroban and/or a pharmaceutically acceptable salt thereof.

In a class of this embodiment, a mole ratio of said 21-(S)-Argatroban to said 21(R) Argatroban is ≥70:30.

In a class of this embodiment, a mole ratio of said 21-(S)-Argatroban to said 21(R) Argatroban is ≥76:23.

In a class of this embodiment, a mole ratio of said 21-(S)-Argatroban to said 21(R) Argatroban is ≥93:7.

In a class of this embodiment, the composition for inhibiting coagulation is prepared in the form of liquid by conventional methods.

The invention provides a novel pharmaceutical composition as thrombin inhibitor for inhibiting coagulation which uses the single diastereoisomer of 21-(S)-Argatroban as active ingredient.

The concentration of active ingredient of the composition is the pharmaceutically acceptable dose of 21(S) Argatroban.

Experiments for measuring the coagulation indices in healthy dogs were conducted with the two diastereoismers of 21-(S)-Argatroban and 21(R) Argatroban. The injections of 21(S) and 21(R) Argatroban were prepared according to the method disclosed in CN200610129330.6. The tested animal was dogs (*Canis familiaris* Linne). Based on the clinical dose of Argatroban, the injected dose was 0.4 mg/Kg, once a day in three consecutive days. The coagulation indices, i.e., Coagulation time of whole blood (CT), recalcification time (RT), kaolin partial thromboplastin time (APTT), pro-time prothrombin time (PT), thrombin time (TT), platelet adhesion rate and platelet aggregation rate were measured before administration and on the third day after administration. Additionally, a control group was set. The measured data was collected and statistically analyzed for determine the experimental results.

The experimental results showed that the single diastereoisomer of 21-(S)-Argatroban of the invention significantly prolonged coagulation time of whole blood (CT), recalcification time (RT), kaolin partial thromboplastin time (APTT), pro-time prothrombin time (PT), thrombin time (TT), and reduced platelet adhesion rate and platelet aggregation rate in healthy dogs. Compared with 21 (R) Argatroban, 21-(S)-Argatroban was twice longer in coagulation time of whole blood (CT), thrice longer in recalcification time (RT), twice longer in pro-time prothrombin time (PT), twice longer in kaolin partial thromboplastin time (APTT), and a litter longer in thrombin time (TT). Compared with the control group, the above-mentioned indices exhibited a significant difference, but there was no significant difference in reducing platelet adhesion rate and platelet aggregation rate.

Therefore, compared with 21 (R) Argatroban, 21-(S)-Argatroban has a stronger effect of inhibiting coagulation and reducing therapeutically effective dose.

The pharmaceutical composition comprising 21-(S)-Argatroban and/or the pharmaceutically acceptable salts thereof of the invention are used as a medicament, and particularly for the treatment and/or prevention of thrombosis or as a platelet aggregation inhibitor.

Advantages of the invention are summarized below:
1) the single diastereoisomer of 21-(S)-Argatroban of the invention significantly prolongs coagulation time of whole blood (CT), recalcification time (RT), kaolin partial thromboplastin time (APTT), pro-time prothrombin time (PT), thrombin time (TT), and reduces platelet adhesion rate and platelet aggregation rate in healthy dogs; and
2) compared with 21 (R) Argatroban, 21-(S)-Argatroban has a stronger effect of inhibiting coagulation and reducing therapeutically effective dose.

DETAILED DESCRIPTION OF THE EMBODIMENTS

For further illustrating the invention, experiments detailing a method for inhibiting coagulation comprising administering to a patient in need thereof a pharmaceutical composition comprising 21-(S)-Argatroban and/or a pharmaceutically acceptable salt thereof are described below. It should be noted that the following examples are intended to describe and not to limit the invention.

EXAMPLE 1

Preparation of 21(S) Argatroban 1) 7 g of Argatroban (R:S=65:35) was added to 210 mL of 85% methanol solution, refluxed under heating for 6.0 hrs, cooled to room temperature, and stood for 5.0 hrs to yield a white crystal. The crystal was filtered, dried at 80° C. to yield 5.6 g of product, of which the content of 21(S) was 42.5% (HPLC).

2) 5 g of Argatroban (R:S=30:70) was added to 100 mL of 50% methanol solution, refluxed under heating for 5.0 hrs, cooled to room temperature, and stood for 4.0 hrs to yield a white crystal. The crystal was filtered, dried to yield 2.5 g of product, of which the content of 21(S) was 85.0% (HPLC).

3) 2 g of Argatroban (R:S=23:76) was added to 60 mL of 20% methanol solution, refluxed under heating for 3.0 hrs, cooled to room temperature, and stood for 3.0 hrs to yield a solid. The solid was filtered, dried to yield 0.9 g of white crystal, of which the content of 21(S) was 94.9% (HPLC).

4) 10 g Argatroban (R:S=7:93) was added to 300 mL of 80% methanol solution, refluxed under heating for 10.0 hrs, cooled to room temperature, and stood for 8.0 hrs to yield a product. The product as the raw material was recrystallized thrice to yield 3.2 g of white crystal, of which the content of 21(S) was 98.1% (HPLC).

The remained mother filtrate was combined, evaporated, and recrystallized to yield 21 (R) Argatroban.

EXAMPLE 2

Preparation of 21(R) and 21-(S)-Argatroban Injection and Animal Tests

Materials:
1. Samples to be Tested:
1) 21-(S)-Argatroban prepared in the step 4) of Example 1 (batch number: 061103)
2) 21(R) Argatroban prepared in Example 1 (batch number: 061102)

3) Colorless and clear liquid: specification, 20 mL: 10 mg; storage: dark, room temperature, and airtight.

2. Reagents:

1) 0.9% NaCl injection: specification, 500 mL; Batch No., D510150401, manufactured by Jinan Sanjiuyimin Pharmaceutical Co. Ltd.

2) Sodium citrate: A.P., specification, 500 g; Batch No., 20021105, manufactured by Shandong Boshan Chemical Reagent Co. Ltd., to be diluted with N. S. to form a solution with concentration of 3.2% for use.

The kits of pro-time prothrombin time, thrombin time, and kaolin partial thromboplastin time are manufactured by Shanghai Taiyang Biotechnology Co. Ltd.

ADP: manufactured by Beijing Dongfangpulisheng Technology & Trade Co. Ltd.

3. Animals:

Dogs: number of 18, half female and half male, weighing 10-15 Kg, and obtained from market.

4. Instrumentations:

HEMAVET-950 automatic globulimeter, manufactured by Drew Scientific Company;

C2000 hemagglutinin meter, manufactured by Beijing Dongfangpulisheng Technology & Trade Co. Ltd;

LBY-NJ2 platelet aggregation meter, manufactured by Beijing Dongfangpulisheng Technology & Trade Company Limited; and Platelet adhesion meter, manufactured by Beijing Dongfangpulisheng Technology & Trade Company Limited.

Test Methods

1. Grouping: 18 dogs were divided into three groups randomly: a control group, an Argatroban (S) injection group, and an Argatroban (R) injection group, each group having 6 dogs.

2. Dose and Basis Thereof:

For an adult, 60 mg of Argatroban are administered by intravenous drip (24 hrs) per day in the first 2 days. In the following 5 days, Argatroban are administered by intravenous drip (3 hrs each time), two times a day, each time 10 mL.

According to the clinical dose of Argatroban for an adult, for a dog, the dose is 0.4 mg/Kg.

3. Preparation of Injections:

0.8 mL of a to-be-tested sample was diluted with 9.2 mL of 0.9% N.S. to yield a solution with concentration of 0.04 mg/ml, and the injected volume of administration was 10 ml/Kg, so the dose was 0.4 mg/Kg.

4. Methods:

The coagulation indices of each dog, e.g. coagulation time of whole blood (CT), recalcification time (RT), kaolin partial thromboplastin time (APTT), pro-time prothrombin time (PT), thrombin time (TT), platelet adhesion rate, and platelet aggregation rate were measured before administration. Subsequently, each group was administered corresponding sample (10 mL/Kg) every day, and once a day for three consecutive days. On the $3^{rd}$ day, the blood of the dogs was collected at 15 minute after administration for measurement.

The measurement of coagulation time of whole blood: 3 test tubes were labeled as No. 1, 2, 3. 3 mL of intravenous blood of the dogs was collected by sterile injectors. Time was started to count when blood entered the injectors. For each test tube, along the wall, 1 mL of blood was pumped slowly and the test tube was put into a water bath at 37° C. To slope No. 1 test tube constantly at a time interval until the blood did not flow even the test tube was placed upside down; then to observe the other two test tubes one by one following the same method. The clotting time of No. 3 test tube was recorded as the coagulation time of whole blood.

The measurement of recalcification time: 1 mL of anticoagulated blood treated with sodium citrate was centrifuged and 0.2 mL of plasma was collected. The plasma was mixed with 0.2 mL of 0.025 mol/L calcium chloride solution and the resultant mixture was put into a water bath at 37° C. The recalcification time is the time interval from the addition of calcium to blood clotting.

The other indices were measured by corresponding instrumentations.

5. Data Statistics and Result Analysis:

All data was expressed as average±SD ($\bar{x}$±SD). Statistical significance between groups was determined by t-test. All comparisons were made based on the control group and significance of difference was expressed as *P<0.05 and **P<0.01.

Experimental results are listed in Tables 1-7.

TABLE 1

Effect of Argatroban injection on coagulation time of whole blood (CT) in healthy dogs ($\bar{x}$ ± SD, n = 6)

| Group | Dose (mg/Kg) | CT before Administration (S) | CT after administration (S) | Variation of CT(S) |
| --- | --- | --- | --- | --- |
| Control group | — | 390.0 ± 70.1 | 375.2 ± 84.1 | −14.8 ± 29.5 |
| S | 0.4 | 390.8 ± 69.3 | 551.8 ± 76.1 | 161.0 ± 102.0** |
| R | 0.4 | 398.7 ± 95.6 | 495.8 ± 91.4 | 97.2 ± 47.9** |

**P < 0.01 compared with the control group.

Compared with the control group, both Argatroban (R) and (S) can obviously prolong the coagulation time of whole blood (CT), and the effect of (S) doubles that of (R).

TABLE 2

Effect of Argatroban injection on recalcification time (RT) in healthy dogs ($\bar{x}$ ± SD, n = 6)

| Group | Dose (mg/Kg) | RT before Administration (S) | RT after administration (S) | Variation of RT(S) |
| --- | --- | --- | --- | --- |
| Control group | — | 126.3 ± 39.4 | 138.5 ± 30.9 | 12.2 ± 18.1 |
| S | 0.4 | 143.2 ± 33.4 | 196.5 ± 31.4 | 53.3 ± 30.5* |
| R | 0.4 | 135.3 ± 33.8 | 154.3 ± 37.1 | 19.0 ± 11.6 |

*P < 0.05 compared with the control group.

Compared with the control group, both Argatroban (R) and (S) can obviously prolong the RT, and the effect of S is about thrice that of R.

TABLE 3

Effect of Argatroban injection on the pro-time prothrombin time (PT) in healthy dogs ($\bar{x}$ ± SD, n = 6)

| Group | Dose (mg/Kg) | PT before Administration (S) | PT after administration (S) | Variation of PT (S) |
| --- | --- | --- | --- | --- |
| Control group | — | 6.2 ± 0.3 | 8.2 ± 1.2 | 2.0 ± 1.0 |
| S | 0.4 | 5.6 ± 0.3 | 9.6 ± 0.7 | 4.0 ± 0.7** |
| R | 0.4 | 6.6 ± 0.3 | 9.0 ± 0.6 | 2.4 ± 0.7 |

**P < 0.01 compared with the control group.

Argatroban (S) can obviously prolong PT, and compared with the control group, significant difference observed (P<0.05 or P<0.01); Argatroban (R) also has a certain effect, but compared with the control group, no significant difference observed (P>0.05). The effect of Argatroban (S) is about twice that of Argatroban (R).

TABLE 4

Effect of Argatroban injection on the thrombin time (TT) in healthy dogs ($\bar{x} \pm SD$, n = 6)

| Group | Dose (mg/Kg) | TT before Administration (S) | TT after administration (S) | Variation of TT (S) |
|---|---|---|---|---|
| Control group | — | 10.4 ± 0.6 | 12.8 ± 1.8 | 2.4 ± 2.0 |
| S | 0.4 | 11.1 ± 0.5 | 53.3 ± 19.2 | 42.2 ± 19.2** |
| R | 0.4 | 10.1 ± 0.7 | 43.1 ± 3.3 | 33.0 ± 3.7** |

**P < 0.01 compared with the control group.

Both Argatroban (R) and (S) can obviously prolong the TT, compared with the control group, significant difference observed (P<0.01) and the effect of Argatroban (S) is a little stronger than that of R.

TABLE 5

Effect of Argatroban injection on the kaolin partial thromboplastin time (APTT) in healthy dogs ($\bar{x} \pm SD$, n = 6)

| Group | Dose (mg/Kg) | APTT before Administration (S) | APTT after administration (S) | Variation of APTT (S) |
|---|---|---|---|---|
| Control group | — | 20.1 ± 1.4 | 21.0 ± 1.9 | 1.0 ± 3.0 |
| S | 0.4 | 20.0 ± 1.0 | 24.5 ± 0.8 | 4.6 ± 1.4* |
| R | 0.4 | 19.8 ± 0.4 | 22.3 ± 2.2 | 2.6 ± 1.8 |

*P < 0.05 compared with the control group.

Argatroban (S) can obviously prolong APTT, and compared with control group, significant difference observed (P<0.05); Argatroban (R) also has a certain effect, but compared with the control group, no significant difference observed (P>0.05). The effect of Argatroban (S) is about twice that of Argatroban (R).

TABLE 6

Effect of Argatroban injection on platelet adhesion rate (PAR) in healthy dogs ($\bar{x} \pm SD$, n = 6)

| Group | Dose (mg/Kg) | PAR before Administration (%) | PAR after administration (%) | Variation of RPAR (%) |
|---|---|---|---|---|
| Control group | — | 30.1 ± 5.3 | 29.5 ± 5.1 | −0.6 ± 3.4 |
| S | 0.4 | 29.6 ± 4.1 | 24.2 ± 3.8 | −5.4 ± 4.4 |
| R | 0.4 | 29.0 ± 4.9 | 24.7 ± 4.6 | −4.3 ± 6.6 |

P > 0.05 compared with the control group.

Both Argatroban (R) and (S) have a reduced effect on platelet adhesion rate, but compared with the control group, no significant difference observed (P>0.05).

TABLE 7

Effect of Argatroban injection on platelet aggregation rate (PAR) in healthy dogs ($\bar{x} \pm SD$, n = 6)

| Group | Dose (mg/Kg) | PAR before Administration (%) | PAR after administration (%) | Variation of RPA (%) |
|---|---|---|---|---|
| Control group | — | 51.2 ± 8.8 | 45.2 ± 6.2 | −6.0 ± 9.0 |
| S | 0.4 | 47.1 ± 4.4 | 42.2 ± 8.6 | −4.9 ± 9.9 |
| R | 0.4 | 51.5 ± 9.9 | 43.5 ± 9.2 | −8.0 ± 13.6 |

P > 0.05 compared with the control group.

Both Argatroban (R) and (S) have a reduced effect on platelet aggregation rate, but compared with the control group, no significant difference observed (P>0.05).

The experimental results show that compared with 21 (R) Argatroban, 21-(S)-Argatroban significantly prolongs coagulation time of whole blood (CT), recalcification time (RT), kaolin partial thromboplastin time (APTT), pro-time pro-thrombin time (PT), thrombin time (TT), and reduces platelet adhesion rate and platelet aggregation rate in healthy dogs.

Compared with the control group, the above-mentioned indices exhibited a significant difference, but there is no significant difference in reducing platelet adhesion rate and platelet aggregation rate.

Therefore, compared with 21 (R) Argatroban, 21-(S)-Argatroban has a stronger effect of inhibiting coagulation and reducing therapeutically effective dose, and more suitable for preparation of pharmaceutical composition inhibiting coagulation.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for inhibiting coagulation, the method comprising administering to a patient in need thereof a pharmaceutical composition comprising 21-(S)-argatroban and 21-(R)-argatroban, wherein mole ratio of 21-(S)-argatroban to 21-(R)-argatroban is in a range of from 70:30 to 85:15.

2. A method for prolonging blood recalcification time, the method comprising administering to a patient in need thereof a pharmaceutical composition, the pharmaceutical composition comprising 21-(S)-argatroban and 21-(R)-argatroban, wherein:
   a mole ratio of 21-(S)-argatroban to 21-(R)-argatroban is 98.1:1.9; and
   a blood recalcification time of the patient is three times longer than a blood recalcification time of a second patient, wherein an equivalent molar amount of pure 21-(R)-argatroban is administered to the second patient.

3. A method for prolonging blood recalcification time, the method comprising:
   a) mixing a pharmaceutical composition comprising 21-(S)-argatroban and 21-(R)-argatroban in saline to obtain a solution, wherein a mole ratio of 21-(S)-argatroban to 21-(R)-argatroban is 98.1:1.9 and a concentration of 21-(S)-argatroban in the solution is 0.04 mg/mL; and
   b) administering the solution obtained in a) to a patient in need thereof.

4. The method of claim 3, wherein a blood recalcification time is three times longer than a blood recalcification time of a second patient, wherein an equivalent molar amount of pure 21-(R)-argatroban is administered to the second patient.

* * * * *